T861050

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED APRIL 29, 1969

861 O.G. 1355

785,042

OXIDATIVE CONVERSION OF ALICYCLIC ALCOHOLS TO KETONES

Charles W. Hargis, James E. Williams, and Howard S. Young, all of P.O. Box 511, Kingsport, Tenn. 37662

Continuation of application Ser. No. 577,147, Sept. 6, 1966. This application Dec. 11, 1968. Published Apr. 29, 1969

Int. Cl. C07c *49/30, 49/44, 49/36*

U.S. Cl. 260—586

No Drawing. 11 Pages Specification

Alicyclic ketones may be produced by passing a vapor-phase mixture of an alicyclic secondary alcohol containing at least 5 carbon atoms, an aromatic hydrocarbon solvent for said alcohol, and an oxygen-containing gas over a silver catalyst at a temperature of from about 300° C. to about 525° C., wherein the oxygen-containing gas provides at least about 100% of the stoichiometric oxygen requirement. The alicyclic ketones so produced are useful intermediates in the manufacture of polymers intended for production of fibers and films.